(12) United States Patent
Suh et al.

(10) Patent No.: US 8,013,599 B2
(45) Date of Patent: Sep. 6, 2011

(54) METHODS AND APPARATUS FOR TESTING A COMPONENT

(75) Inventors: Ui Won Suh, Cincinnati, OH (US); Gigi Olive Gambrell, West Chester, OH (US); John William Ertel, New Vienna, OH (US); William Stewart McKnight, Hamilton, OH (US)

(73) Assignee: General Electric Company, Schenectady, NY (US)

( * ) Notice: Subject to any disclaimer, the term of this patent is extended or adjusted under 35 U.S.C. 154(b) by 479 days.

(21) Appl. No.: 10/993,467

(22) Filed: Nov. 19, 2004

(65) Prior Publication Data

US 2006/0109001 A1  May 25, 2006

(51) Int. Cl.
*G01N 27/82* (2006.01)
(52) U.S. Cl. .................. 324/240; 324/232; 324/238
(58) Field of Classification Search .......... 324/238, 324/240, 232
See application file for complete search history.

(56) References Cited

U.S. PATENT DOCUMENTS

| | | | |
|---|---|---|---|
| 4,591,784 A | 5/1986 | Kolitsch et al. | |
| 4,628,261 A | 12/1986 | Huschelrath et al. | |
| 4,821,204 A | 4/1989 | Huschelrath | |
| 5,028,100 A | 7/1991 | Valleau et al. | |
| 5,182,775 A | 1/1993 | Matsui et al. | |
| 5,291,136 A * | 3/1994 | Van der Veer et al. | 324/262 |
| 5,329,230 A | 7/1994 | Viertl et al. | |
| 5,334,934 A | 8/1994 | Viertl | |
| 5,345,514 A | 9/1994 | Mahdavieh et al. | |
| 5,430,376 A | 7/1995 | Viertl | |
| 5,670,879 A | 9/1997 | Zombo et al. | |
| 6,040,695 A | 3/2000 | Raulerson et al. | |
| 6,288,537 B1 | 9/2001 | Viertl et al. | |
| 6,339,326 B1 | 1/2002 | Trantow | |
| 6,356,069 B1 | 3/2002 | Trantow et al. | |
| 6,433,541 B1 | 8/2002 | Lehman et al. | |
| 6,452,384 B1 | 9/2002 | Becker et al. | |
| 6,515,623 B2 | 2/2003 | Johnson | |
| 6,532,840 B2 | 3/2003 | Hatley et al. | |
| 6,621,264 B1 | 9/2003 | Lehman et al. | |

(Continued)

FOREIGN PATENT DOCUMENTS

EP          0136238          3/1989

(Continued)

OTHER PUBLICATIONS

H. Fenniri, A. Moineau, G. Delaunay; "Profile Imagery Using a Flat Eddy-Current Proximity Sensor"; 1994 Elsevier Science S.A.; 183-190.

(Continued)

*Primary Examiner* — Patrick J Assouad
*Assistant Examiner* — David M. Schindler
(74) *Attorney, Agent, or Firm* — David J. Clement, Esq.; Armstrong Teasdale LLP

(57) ABSTRACT

A method for inspecting a component having a surface profile that includes a local minima and a local maxima. The method includes positioning an eddy current probe proximate to a surface of the component to generate a first position indication, positioning the eddy current probe proximate to the surface of the component to generate a second position indication that is different than the first position indication, and interpolating between the first and second position indications to determine a profile of a portion of the surface of the component.

11 Claims, 10 Drawing Sheets

U.S. PATENT DOCUMENTS

| | | |
|---|---|---|
| 6,745,622 B2 | 6/2004 | Smith et al. |
| 6,888,347 B2 | 5/2005 | Batzinger et al. |
| 6,894,492 B1 | 5/2005 | Dziech |
| 6,907,358 B2 | 6/2005 | Suh et al. |
| 7,005,851 B2 | 2/2006 | May et al. |
| 7,026,811 B2 | 4/2006 | Roney, Jr. et al. |
| 7,070,476 B2 | 7/2006 | Lehman et al. |
| 7,190,162 B2 | 3/2007 | Tenley et al. |
| 7,233,867 B2 | 6/2007 | Pisupati et al. |
| 2001/0017540 A1* | 8/2001 | Arai .................... 324/236 |
| 2003/0169035 A1* | 9/2003 | Crouzen ................. 324/230 |
| 2004/0153260 A1* | 8/2004 | Suh et al. .................. 702/38 |

FOREIGN PATENT DOCUMENTS

| | | |
|---|---|---|
| EP | 0533440 A1 | 3/1993 |
| EP | 0924516 A2 | 6/1999 |
| EP | 0924516 A2 | 6/1999 |
| EP | 1029237 A1 | 8/2000 |
| EP | 1052505 A1 | 11/2000 |
| EP | 1111379 B1 | 6/2006 |
| JP | 61264201 | 11/1986 |
| JP | 5240840 A | 9/1993 |
| JP | 11248685 A | 9/1999 |
| JP | 2001183348 A | 7/2001 |
| JP | 2001522046 T | 11/2001 |
| WO | 9923484 A1 | 5/1999 |
| WO | 03003040 A2 | 1/2003 |

OTHER PUBLICATIONS

International Search Report; Dated Jul. 10, 2006; Application 05257104.9-2204; Place of Search—Munich; 14 pgs.

International Search Report; Application No./Patent No. 05257104.9-2204; Place of Search Munich; Dated Feb. 22, 2006; 6 pgs.

* cited by examiner

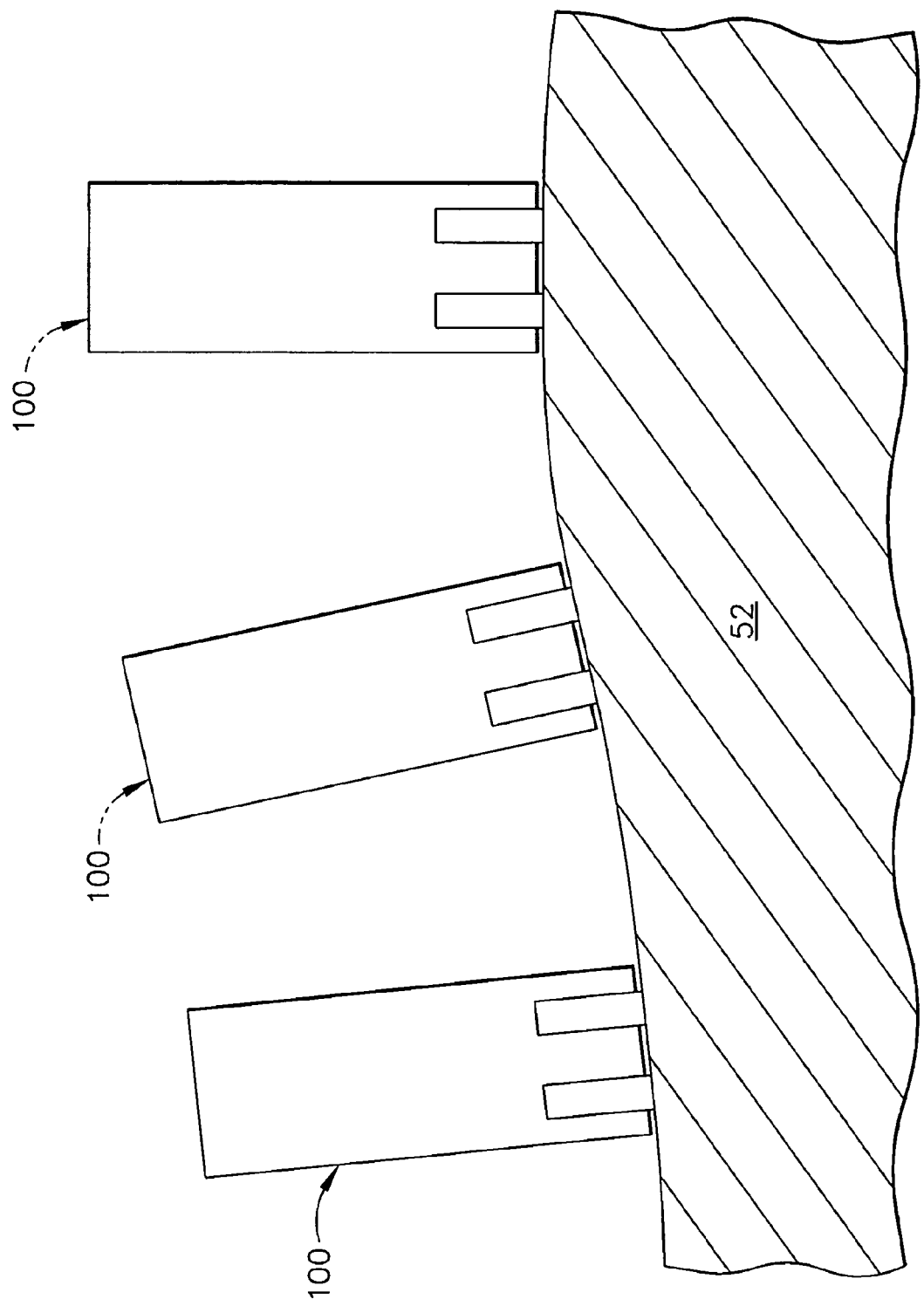

METHODS AND APPARATUS FOR TESTING A COMPONENT

BACKGROUND OF THE INVENTION

This invention relates generally to the testing of components, and more particularly to methods and apparatus for testing components having non-uniform surfaces.

Eddy current (EC) inspection devices are used to detect abnormal indications in a component under test such as, but not limited to, a gas turbine engine component. At least one known EC inspection device is used to detect cracks, pings, dings, raised material, and/or other surface imperfections on a surface of the component, and/or to evaluate material properties of the component including the conductivity, density, and/or degrees of heat treatment of the component.

During operation, known EC devices measure the interaction between an electromagnetic field generated by the EC device and the component being tested. For example, known EC devices include a probe coil that generates a magnetic field. When the coil is positioned adjacent to a conductive component, an eddy current is generated on the surface of the component. A flaw on and/or near the surface of the component generates a disruption in the eddy current field which produces a secondary field that is received by the eddy current probe coil or by a sensor coil in the eddy current probe which converts the altered secondary magnetic field to an electrical signal that may be recorded on a strip chart recorder for example.

At least one known EC device includes a relatively small coil that is typically 0.020 inches in diameter, that is used to detect surface flaws, surface contamination, material properties, and/or a surface roughness of the component being tested. In use, a substantially constant pressure is applied to the probe as the coil moves along the surface of the component under test to facilitate maintaining an integrity of the signal generated by the EC device. However, when the EC device is not oriented normal to the surface of the component being tested, a "lift-off effect" may be created To facilitate reducing the lift-off-effect, at least one known EC device includes a dual-coil probe, e.g. a differential probe, having a pair of coils with an opposite polarity. Each coil in the dual-coil probe generates an electrical signal when the probe contacts a surface of the component being tested. When the dual coil probe passes over a smooth surface of the component being tested, the signals cancel each other. However, when the dual coil probe passes over a local physical abnormality on the surface, the probe generates a signal that is proportional to the size, depth, etc., of the physical abnormality.

When a non-continuous component surface feature is inspected, such as a feature on a rotating part, known differential probes may have difficulty resolving sharp curvatures, in such areas as corners and cusps. During operation, when such probes encounter a corner or cusp, the differential probe device may become skewed to the surface of the component, such that a resulting lift-off effect may cause a loss of usable data. Accordingly, known EC devices may be less effective in generating an accurate response when the EC device is used to detect an abnormal condition on a component having complex geometries, and/or a component having irregular conditions, especially in components including sharp indexing or objects that extend into the path of the probe such that the probe cannot consistently be placed normal to scan surface.

BRIEF DESCRIPTION OF THE INVENTION

In one aspect, a method for inspecting a component is provided. The method includes positioning an eddy current probe proximate to a surface of the component to generate a first position indication, positioning the eddy current probe proximate to the surface of the component to generate a second position indication that is different than the first position indication, and interpolating between the first and second position indications to determine a profile of a portion of the surface of the component.

In another aspect, a differential eddy current probe for inspecting a component is provided. The eddy current probe includes a body portion including an outer surface and having a width, and a length that is longer than the width, and a tip portion extending from the body portion, the tip portion including an end and an outer tip, the end extending between the body portion and the outer tip, the tip portion having a width and a length, the tip portion width gradually decreases from the tip portion end to the outer tip, the tip portion length gradually decreases from the tip portion end to the outer tip, and at least two differential coils mounted within said tip portion, each of said at least two coils comprises a substantially cylindrical shape, at least a portion of each of said at least two coils is positioned adjacent to said tip portion outer tip for generating a magnetic field that is substantially perpendicular to a surface of the component being inspected.

In a further aspect, an eddy current inspection system is provided. The inspection system includes a differential eddy current probe and a computer coupled to the eddy current probe. The computer is configured to position the eddy current probe proximate to a surface of a component to generate a first position indication, position the eddy current probe proximate to the component surface to generate a second position indication that is different than the first position indication, and interpolate between the first and second position indications to determine a profile of a portion of the component surface.

BRIEF DESCRIPTION OF THE DRAWINGS

FIG. 14 illustrates the eddy current probe shown in FIG. 7 positioned normal to a surface of a component.

DETAILED DESCRIPTION OF THE INVENTION

Figure 1:
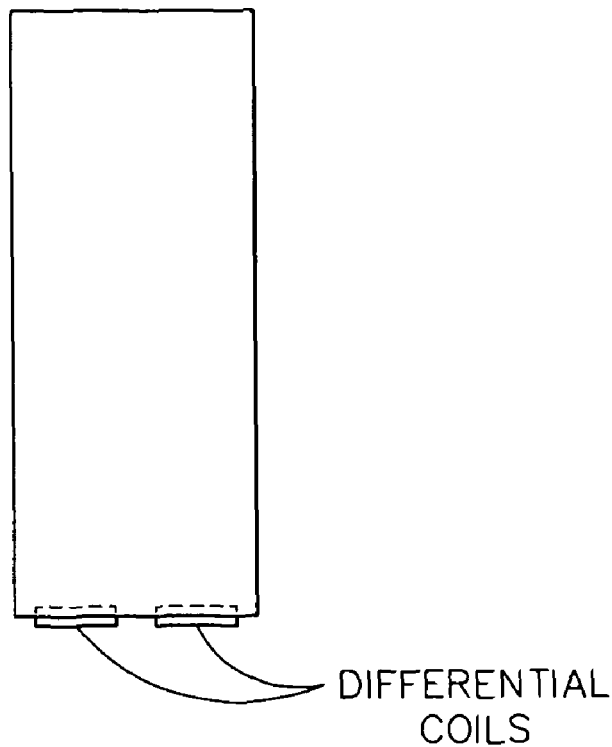
FIG. 1 is a front view of a known eddy current probe.
Figure 2:
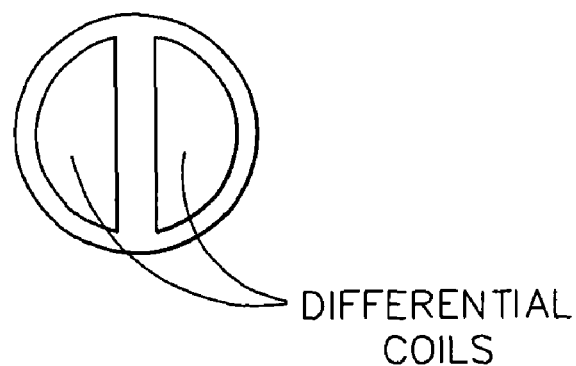
FIG. 2 is a top view of the known eddy current probe shown in FIG. 1.
Figure 3:
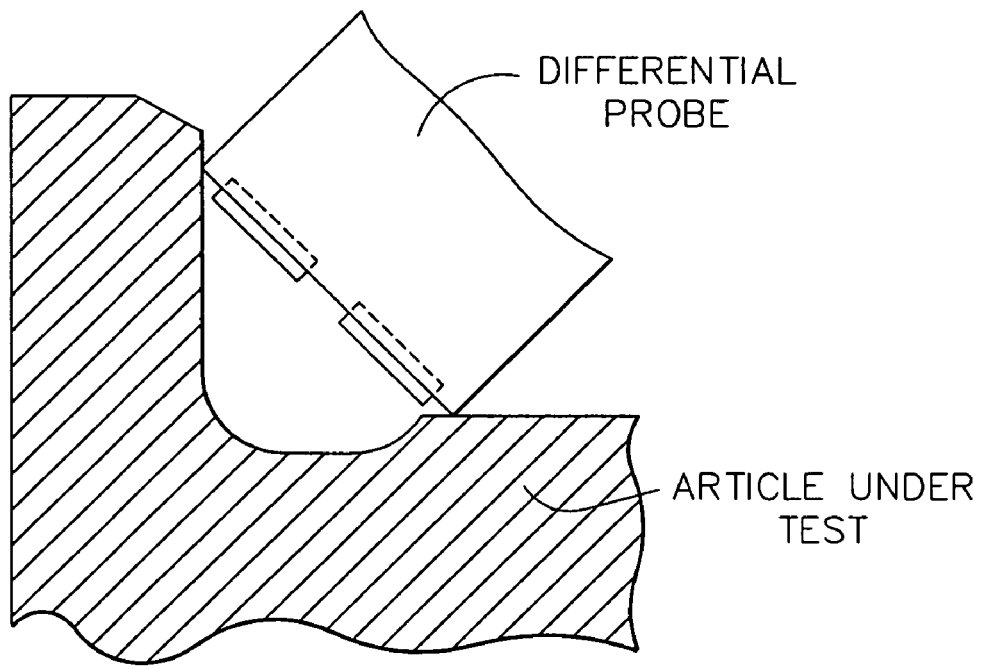
FIG. 3 is a front view of the known eddy current probe shown in FIG. 1 illustrating a lift-off effect in an indexing direction.
Figure 4:
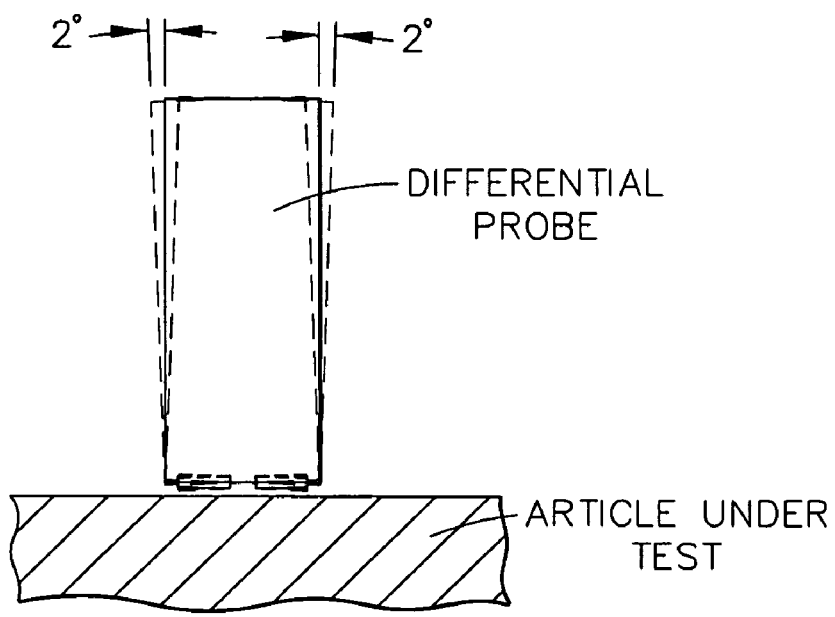
FIG. 4 is a front view of the known eddy current probe shown in FIG. 1 and illustrating a lift-off effect in a scan direction.

FIG. 1 is a front view of a known eddy current probe 500. FIG. 2 is a top view of eddy current probe 500 shown in FIG. 1. FIG. 3 is a front view of eddy current probe 500 shown in FIG. 1 illustrating a lift-off effect in an indexing direction. FIG. 4 is a front view of eddy current probe 500 shown in FIG. 1 and illustrating a lift-off effect in a scan direction.

Figure 5:
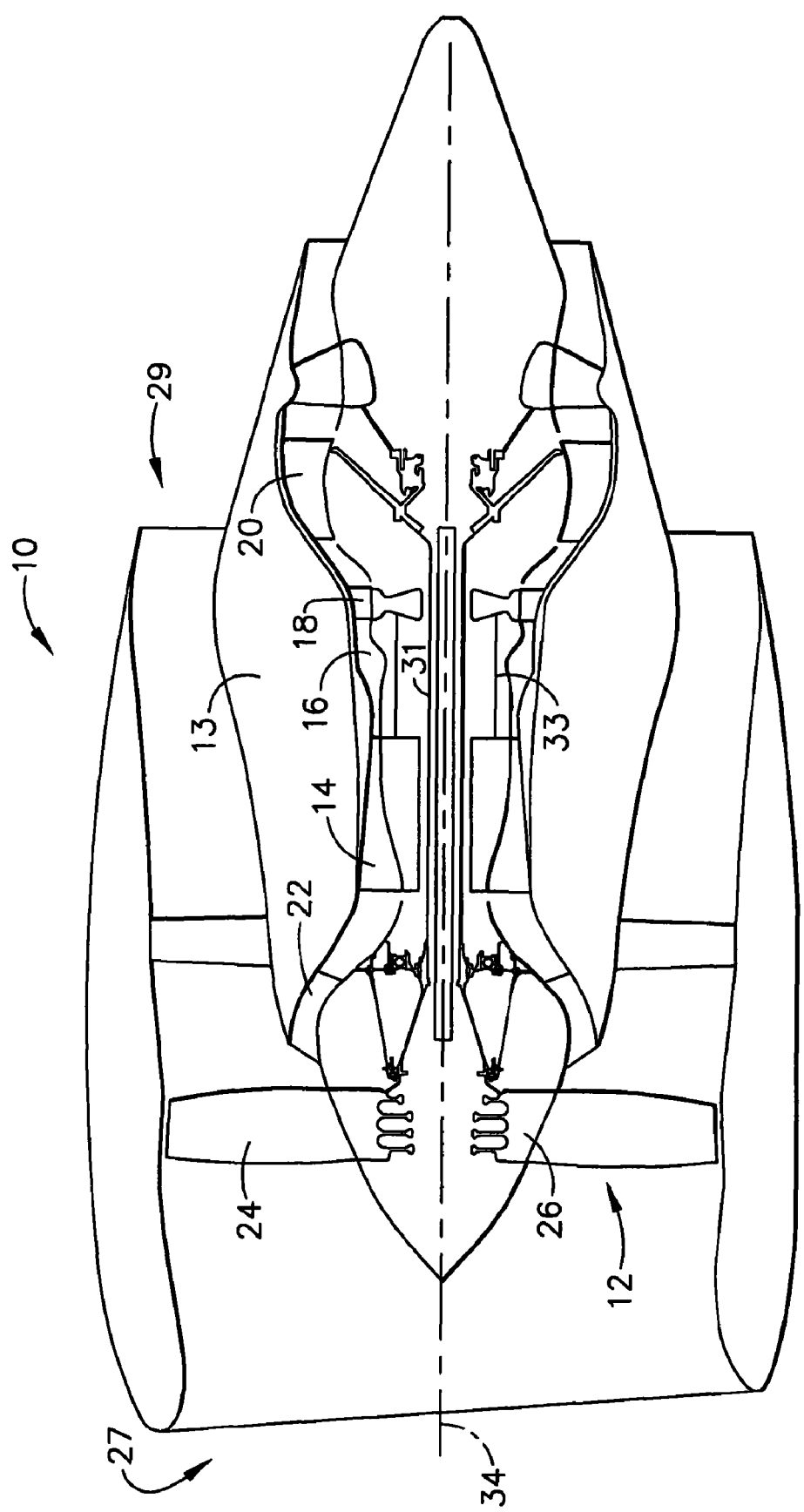
FIG. 5 is a schematic illustration of an exemplary gas turbine engine.

FIG. 5 is a schematic illustration of a gas turbine engine 10 including a fan assembly 12 and a core engine 13 including a high pressure compressor 14, and a combustor 16. Engine 10 also includes a high pressure turbine 18, a low pressure turbine 20, and a booster 22. Fan assembly 12 includes an array of fan blades 24 extending radially outward from a rotor disc 26. Engine 10 has an intake side 27 and an exhaust side 29. In one embodiment, the gas turbine engine is a CF6-50 available from General Electric Company, Cincinnati, Ohio. Fan assembly 12 and turbine 20 are coupled by a first rotor shaft 31, and compressor 14 and turbine 18 are coupled by a second rotor shaft 33.

During operation, air flows axially through fan assembly 12, in a direction that is substantially parallel to a central axis 34 extending through engine 10, and compressed air is supplied to high pressure compressor 14. The highly compressed air is delivered to combustor 16. Airflow (not shown in FIG. 1) from combustor 16 drives turbines 18 and 20, and turbine 20 drives fan assembly 12 by way of shaft 31.

Figure 6:
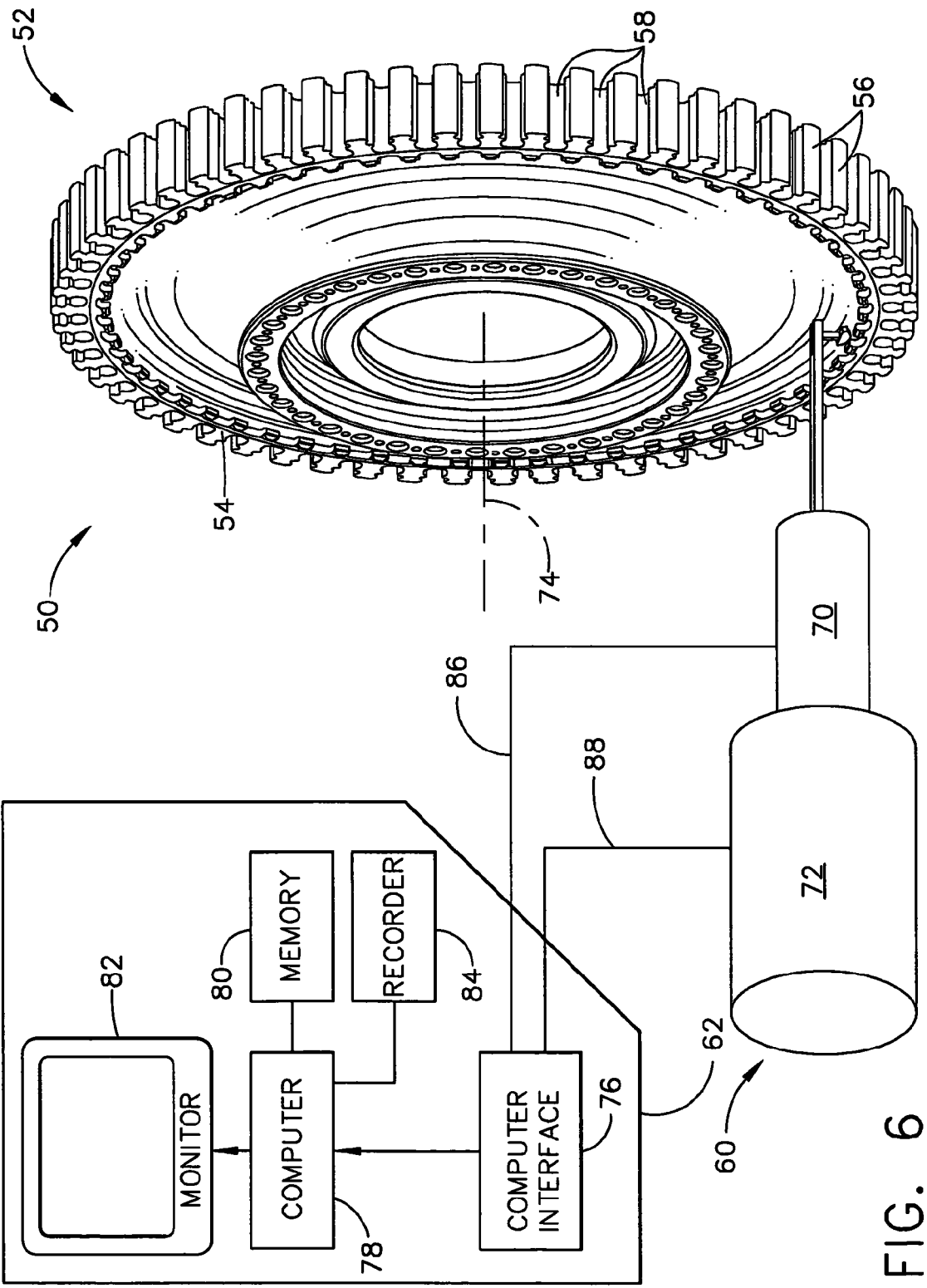
FIG. 6 is a schematic diagram of an exemplary eddy current surface flaw detection system.

FIG. 6 is a schematic diagram of an exemplary eddy current surface flaw detection system 50 that can be used to inspect a component 52 such as, but not limited to, a gas turbine engine disk 54 which may be used with gas turbine engine 10. In the exemplary embodiment, disk 54 includes a plurality of dovetail posts 56 and a plurality of dovetail slots 58 defined between posts 56.

Although the methods and apparatus herein are described with respect to posts 56 and dovetail slots 58, it should be appreciated that the methods and apparatus can be applied to a wide variety of components. For example, component 52 may be of any operable shape, size, and configuration. Examples of components may include, but are not limited to, components of gas turbine engines such as seals, flanges, turbine blades, turbine vanes, and/or flanges. The component may be fabricated of any operable base material such as, but not limited to, nickel-base alloys, cobalt-base alloys, titanium-base alloys, iron-base alloys, and/or aluminum-base alloys. More specifically, although the methods and apparatus herein are described with respect to aircraft engine parts, it should be appreciated that the methods and apparatus can be applied to a wide variety of components used within a steam turbine, a nuclear power plant, an automotive engine, or to inspect any mechanical components.

In the exemplary embodiment, detection system 50 includes a probe assembly 60 and a data acquisition/control system 62. Probe assembly 60 includes an eddy current coil/probe 70 and a probe manipulator 72. Eddy current probe 70 and probe manipulator 72 are each electrically coupled to data acquisition/control system 62 such that control/data information can be transmitted to/from eddy current probe 70/probe manipulator 72 and data acquisition/control system 62. In an alternative embodiment, system 50 also includes a turntable (not shown) configured to rotate component 52 around a central axis 74 during the inspection procedure.

Data acquisition/control system 62 includes a computer interface 76, a computer 78, such as a personal computer with a memory 80, and a monitor 82. Computer 78 executes instructions stored in firmware (not shown). Computer 78 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Memory 80 is intended to represent one or more volatile and/or nonvolatile storage facilities that shall be familiar to those skilled in the art. Examples of such storage facilities often used with computer 78 include, but are not limited to, solid state memory (e.g., random access memory (RAM), read-only memory (ROM), and flash memory), magnetic storage devices (e.g., floppy disks and hard disks), and/or optical storage devices (e.g., CD-ROM, CD-RW, and DVD). Memory 80 may be internal to or external to computer 78. Data acquisition/control system 62 also includes a recording device 84 such as, but not limited to, a strip chart recorder, a C-scan, and an electronic recorder that is electrically coupled to either computer 78 and/or eddy current probe 70.

In use, component 52, such as disk 54, is mounted on a fixture (not shown) to secure disk 54 in place during inspection. Eddy current probe 70 is coupled to probe manipulator 72 to position probe 70 within dovetail slots 58 to facilitate enabling substantially all of the interior of dovetail slots 58 to be scanned during inspection. In the exemplary embodiment, probe manipulator 72 is a six-axis manipulator. Eddy current probe 70 is electrically coupled to data acquisition/control system 62 by a data link 86. Eddy current probe 70 generates electrical signals in response to the eddy currents induced within the surface of dovetail slots 58 during scanning of dovetail slots 58 by probe 70. Electrical signals generated by probe 70 are received by data acquisition/control system 62 over a data communications link 86 and are either stored in memory 80 or recorder 84. Computer 78 is also interconnected to probe manipulator 72 by a communications link 88 to facilitate controlling the scanning of disk 54. A keyboard (not shown) is electrically coupled to computer 78 to facilitate operator control of the inspection of disk 54. In the exemplary embodiment, a printer 40 may be provided to generate hard copies of the images generated by computer 78.

Figure 7:
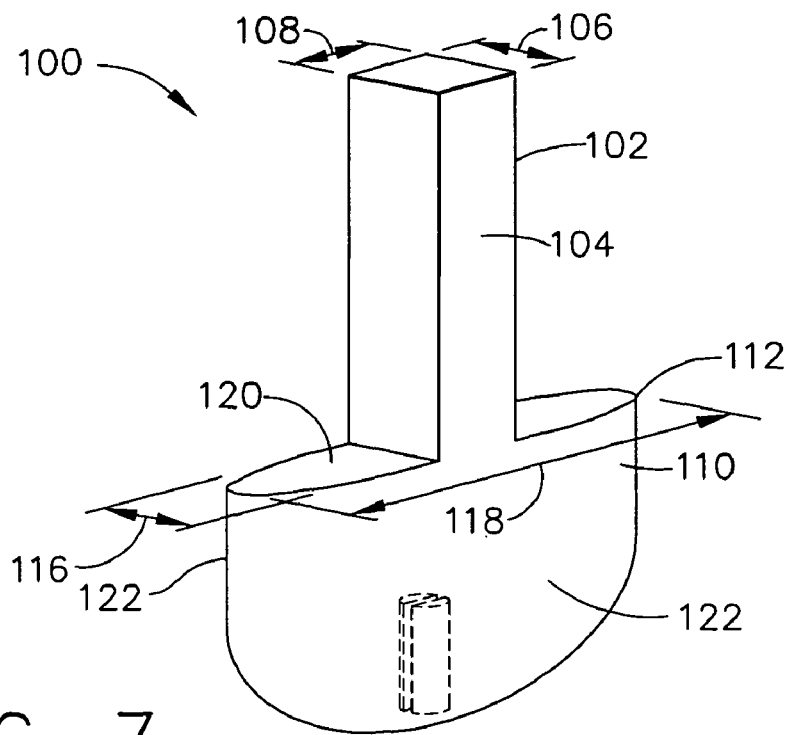
FIG. 7 is a perspective view of an exemplary eddy current probe.
Figure 8:
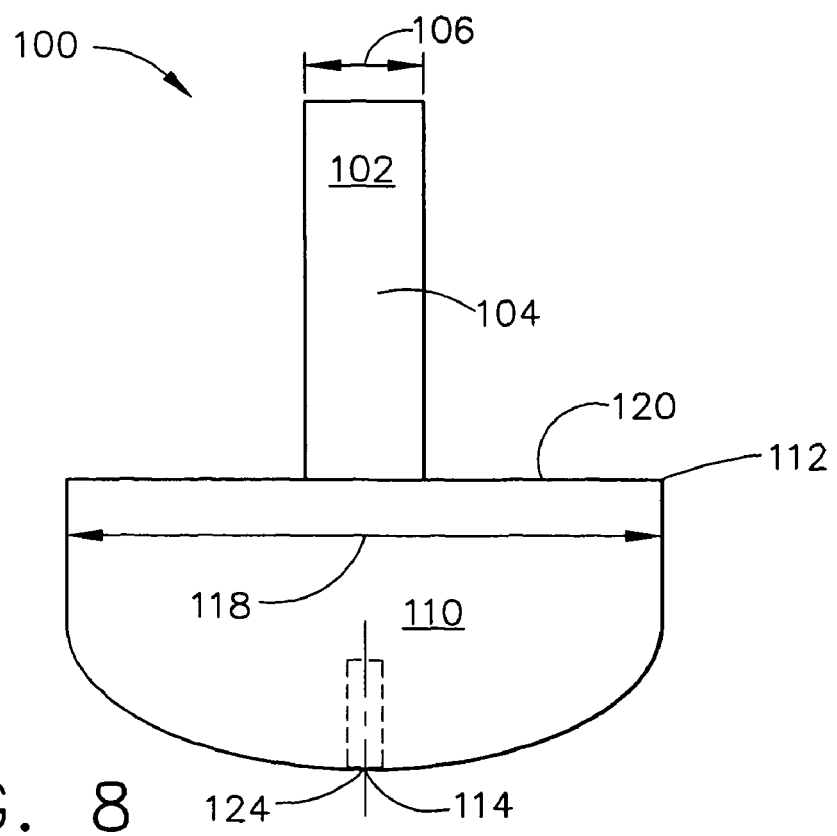
FIG. 8 is a front view of the exemplary eddy current probe shown in FIG. 7.
Figure 9:
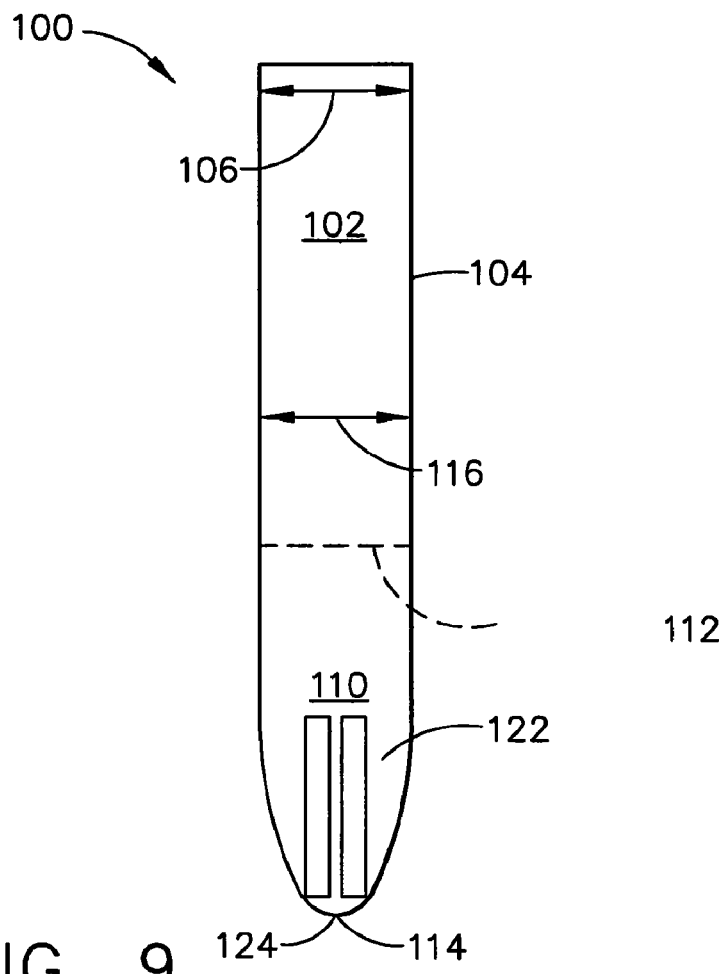
FIG. 9 is a side view of the exemplary eddy current probe shown in FIG. 7.
Figure 10:
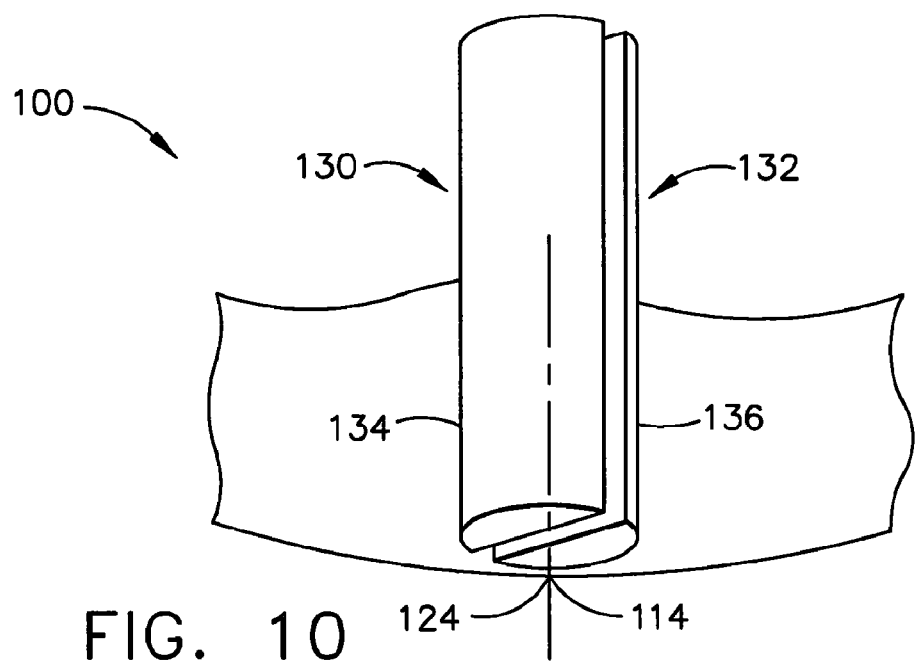
FIG. 10 is a perspective view of the differential coils in the exemplary eddy current probe shown in FIG. 7.

FIG. 7 is a perspective view of an exemplary eddy current probe 100 that may be used with eddy current surface flaw detection system 50 (shown in FIG. 6). FIG. 8 is a front view of eddy current probe 100. FIG. 9 is a side view of eddy current probe 100. FIG. 10 is a perspective view of a portion of eddy current probe 100. In the exemplary embodiment, eddy current probe 100 is a differential probe.

Eddy current probe 100 includes a body portion 102 that includes an outer surface 104, a width 106, and a length 108 that is different than width 106. In the exemplary embodiment, body portion 102 is substantially rectangular shaped. Eddy current probe 100 also includes a tip portion 110 that is coupled to body portion 102. In the exemplary embodiment, body portion 102 and tip portion 110 are integrally formed together such that body portion 102 and tip portion 110 form a unitary eddy current probe 100.

Tip portion 110 includes a tip body portion end 112 and a outer tip 114. Tip portion 110 has a width 116 and a length 118 that is greater than width 116. In the exemplary embodiment, width 116 gradually decreases from tip body portion end 112 to outer tip 114, and length 118 gradually decreases from tip body portion end 112 to outer tip 114.

Tip portion 110 also includes an upper surface 120 that is coupled to body 102. In the exemplary embodiment, tip upper surface 120 includes a substantially rectangular surface defined such that tip portion width 116 is substantially similar to body portion width 106, and tip portion length 118 is substantially greater than body length 108. In the exemplary embodiment, tip width 116 and tip length 118 each gradually diminish from tip upper surface 120 such that an apex 124 is formed at outer tip 114.

Eddy current probe 100 also includes a first probe coil 130 and a second probe coil 132 mounted within tip portion 110. Probe coils 130 and 132 each include respective substantially flat outer surfaces 134 and 136 such that the outer surfaces of probe coils 130 and 132 are positioned coincident with the outer tip 114. In the exemplary embodiment probe coils 130 and 132 are differential coils. When activated, coils 130 and 132 each generate a magnetic field that is substantially perpendicular to a surface of the component being scanned such as, but not limited to posts 56 and dovetail slots 58. More specifically, each coil 130, 132 in differential probe 100 generates an electrical signal when probe 100 contacts a surface of the component being tested. When differential probe 100 passes over a smooth surface of the component being tested, the signals cancel each other. However, when differential probe 100 passes over a local physical abnormality on the surface, differential probe 100 generates a signal that is proportional to the size, depth, etc., of the physical abnormality.

Eddy current probe 100 has a length 118 that is longer than a gap defined between inspection areas in the scan direction, and a width 116 that is shorter in the indexing direction. The indexing direction refers to the direction eddy current probe 100 is moved in order to repeat the scanning process at a new position. Coils 130 and 132 are positioned approximately in the center of tip portion 110. Accordingly, eddy current probe 100 includes an approximately spade-shaped tip portion 110 that enables gaps between inspection areas to be traversed without by tip portion 110 falling into the gaps. Moreover, and in the exemplary embodiment, the relatively round bottom of outer tip 114 facilitates coils 130 and 132 being fabricated with a radius of approximately 25 mils. The relatively small size of eddy current probe 100 facilitates probe 100 maintaining a substantially normal contact with relatively sharply contoured surfaces.

Figure 11:
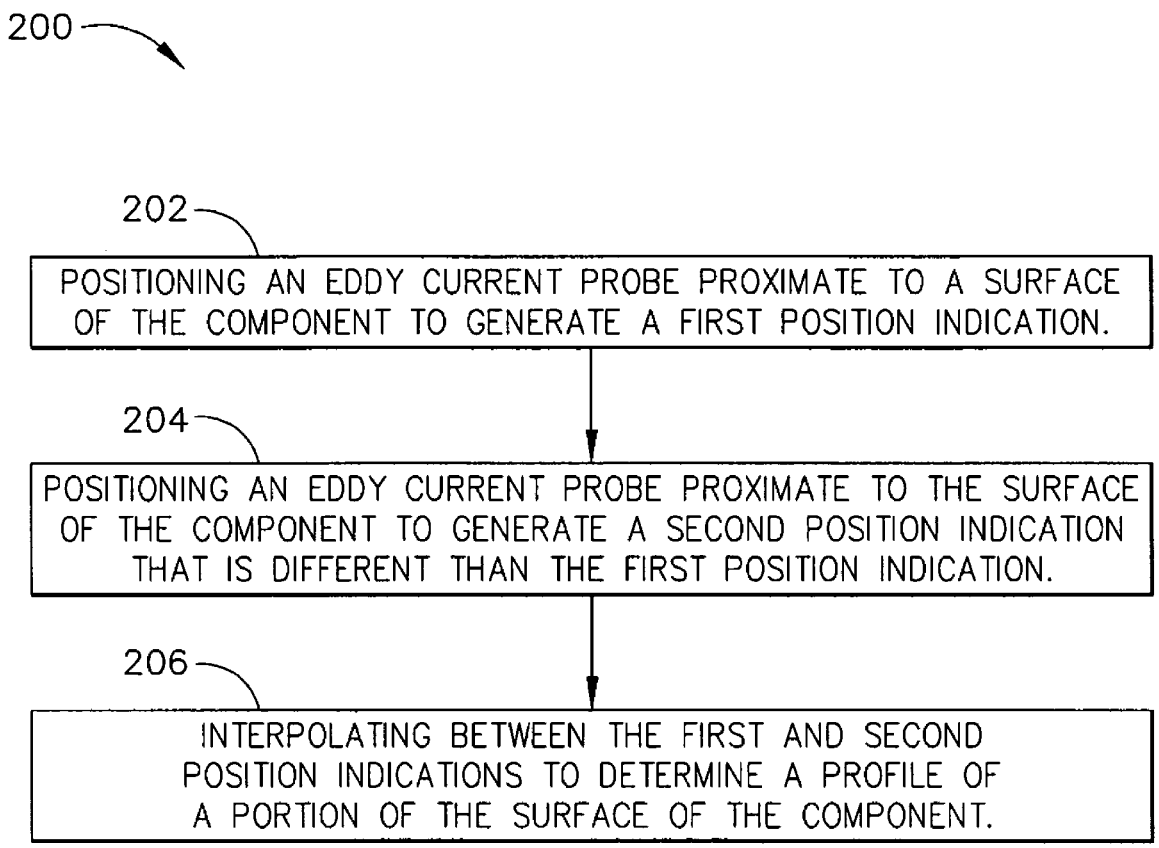
FIG. 11 is a flowchart illustrating an exemplary method for performing an eddy current inspection.
Figure 12:
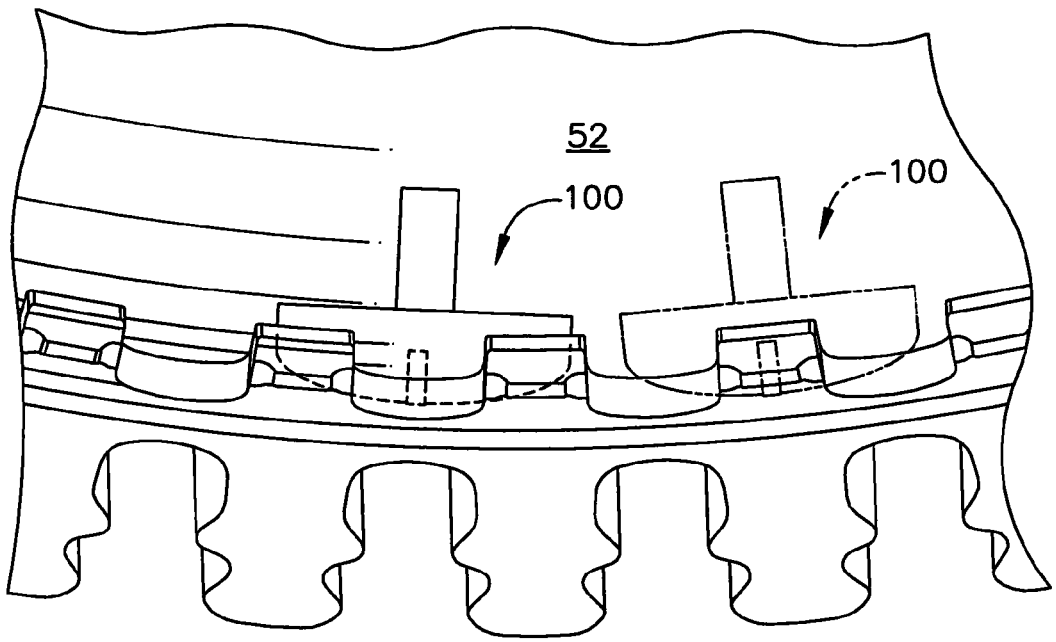
FIG. 12 is a side view of an eddy current probe operating in a scan direction.
Figure 13:
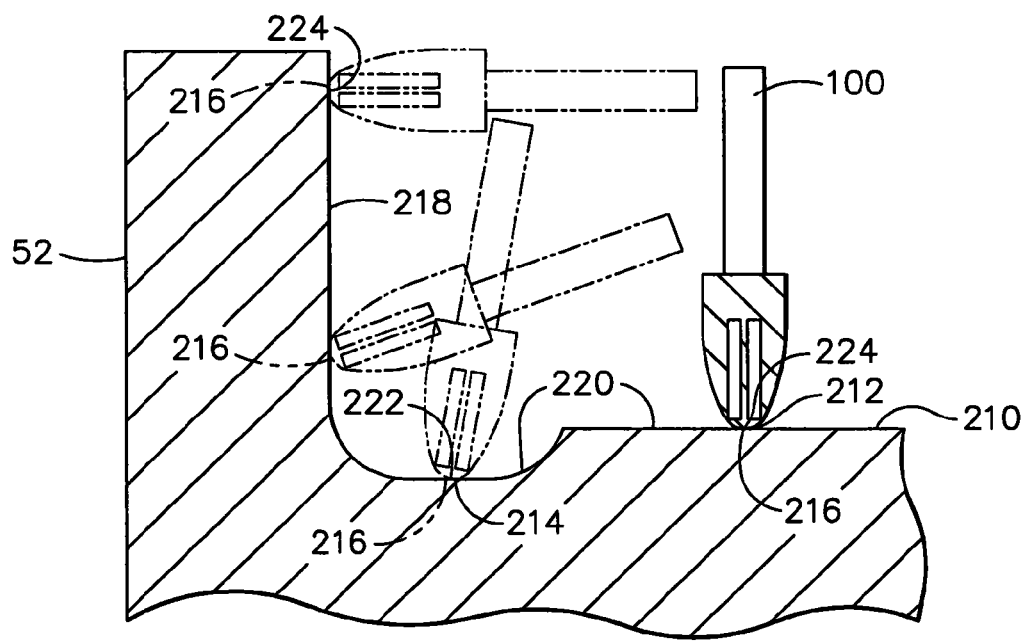
FIG. 13 is a side view of an eddy current probe operating in an indexing direction.

FIG. 11 is a flow chart illustrating an exemplary method 200 for inspecting a component having a surface that includes a local minima and a local maxima. FIG. 12 is a side view of an eddy current probe operating in a scan direction. FIG. 13 is a side view of an eddy current probe operating in an indexing direction.

Method 200 includes positioning 202 an eddy current probe proximate to a surface of the component to generate a first position indication, positioning 204 the eddy current probe proximate to the surface of the component to generate a second position indication that is different than the first position indication, and interpolating 206 the first and second position indications to determine a profile of a portion of the surface of the component.

During operation, eddy current surface flaw detection system 50 is operated such that eddy current probe 100 is positioned on or near a surface 210 of component 52 to generate a first position indication 212. More specifically, eddy current probe 100 is positioned normal to surface (+/−2 degrees) 210 until a signal is acquired from eddy current probe 100 as shown in FIG. 14. Eddy current surface flaw detection system 50 is then operated such that eddy current probe 100 is positioned on or near surface 210 of component 52 to generate a second position indication 214 that is different than the first position indication 212. In the exemplary embodiment, eddy current probe 100 is positioned normal to component surface 210 at a plurality of positions 216 on component surface 210 and repositioned in the probe indexing direction to generate the plurality of position indications 216. Although the exemplary embodiment, illustrates four position indications 216, it should be realized that eddy current surface flaw detection system 50 may position eddy current probe 100 at any quantity of position indications without affecting the scope of the method described herein.

Plurality of position indications 216 are each sent to computer 78 for example for further processing. More specifically, position indications 216 are utilized by computer 78 to determine a surface profile 218 of component 52. In operation, at least first position indication 212 and second position indication 214 are interpolated to generate a plurality of positions 220 between first and second position indications 212 and 214, respectively. Plurality of positions 220 are then utilized with first and second position indications to determine a surface profile 218 of component 52. More specifically, in the exemplary embodiment, component 52 includes a relatively non-uniform exterior surface 210. Accordingly, eddy current probe 100 is positioned at or near surface 210 at a plurality of points or positions 216 until a plurality of eddy current readings are generated. Computer 78 receives the plurality of points or positions 216 and interpolates between each respective point/position 216 to generate a profile of component surface 210. In the exemplary embodiment, plurality of positions 216 includes at least one minima 222 and at least one maxima 224. More specifically, in the exemplary embodiment, component 52 includes a surface 210 that is substantially non-linear, i.e. contoured. Accordingly, eddy current probe 100 is positioned at a plurality of points or positions 216, including minima and maxima positions 222 and 224 to facilitate ensuring the any local maxima or minima on the component surface is recorded and sent to computer 78. Computer 78 receives the plurality of points or positions 216 and interpolates between each respective point/position 216 to generate a profile of component surface 210. The component surface profile 218 is then utilized by computer 78 to generate a scan plan for component 52.

Figure 15A:
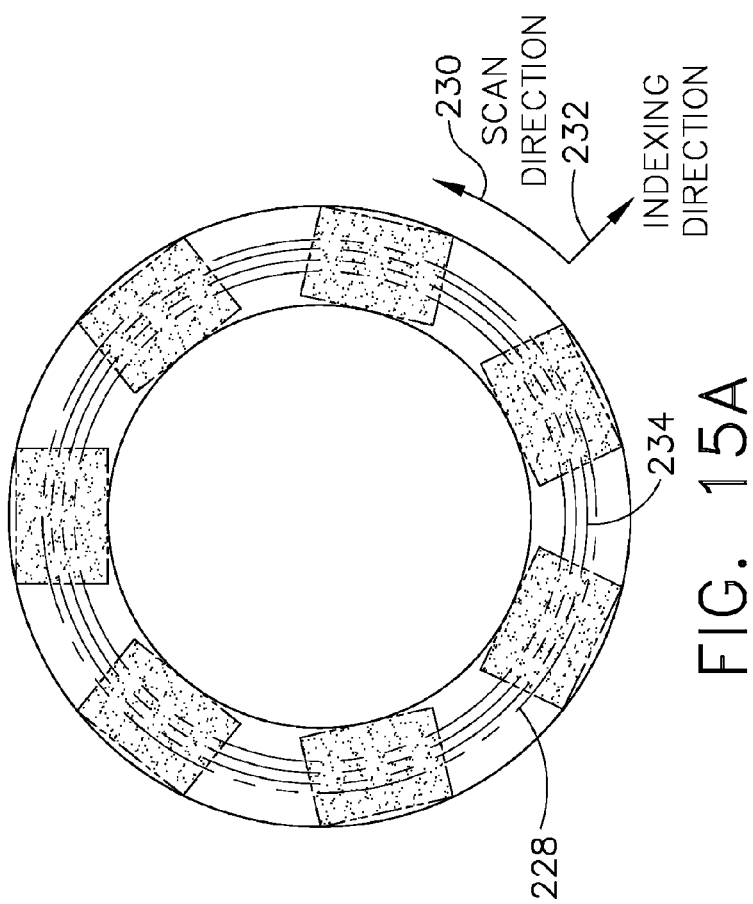
FIGS. 15a and 15b illustrate a scanplan and C-scan images created by scanning a differential eddy current probe.
Figure 15B:
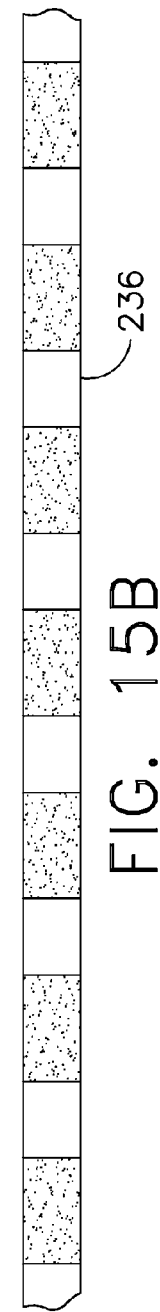

In the exemplary embodiment, computer 78 receives the plurality of position indications and generates a scan plan. Generating a scan plan includes generating a scan plan to facilitate directing eddy current probe 100 to scan an inspection area. Scanplan as used herein is defined as a collection of Computer Numeric Control (CNC) commands that direct probe 100 to move along a predetermined line 228 in the scan direction 230 (shown in FIG. 15a) while acquiring a signal from eddy current probe 100. At the completion of each scan line, eddy current probe 100 is indexed 232 or moved to the next scan line 234 (shown in FIG. 15a) and eddy current probe 100 again is moved along a predetermined line 234 in the scan direction 230. More specifically, computer 78 includes the component profile that is generated utilizing plurality of points or positions 216 and interpolating between each respective point/position 216. Therefore, computer 78 moves or indexes eddy current probe 100 along the profile 218 that is previously generated. This process is continued until the scan plan is completed. FIGS. 15a and 15b illustrate a scan plan using eddy current probe 100 wherein scan line 228 of 360° circumferential rotation, and a two-dimensional image 236 of the component being inspected, are illustrated.

In the exemplary embodiment, eddy current probe 100 requires contacting the surface of the component being inspected without unwanted lift-off, whereas at least one known eddy current probe has difficulty scanning a component that includes a highly contoured outer surface. Designing a scan plan that is implemented using a known eddy current probe is relatively time consuming since the designer must incorporate expected occurrences of probe lift-off into the scan plan prior to scanning the component. Therefore generating a scanplan that utilizes a predetermined component surface profile facilitates maintaining the eddy current probe in a vertical position that is substantially normal to a surface of the component being tested. Accordingly, maintaining the eddy current probe substantially normal to the surface of the component being tested facilitates reducing and/or eliminating the lift-off effect during the scanning procedure.

In operation, coupling an eddy current probe, such as probe 100, to an eddy current inspection system includes coupling eddy current probe 100 to probe holder such as probe manipulator 72 (shown in FIG. 6). A rotation axis is then set to zero degrees before the scan starts. The component 52 is then scanned using eddy current probe 100 based on the scan plan to generate a plurality of scan data. Specifically, eddy current inspection system 50 is activated such that the component is scanned in the scanning direction by turning the rotary axis while the probe stays at a fixed position. Eddy current probe 100 then rides over any interrupted gaps on the component until the scan is completed in the scanning direction. At the next zero degree point of rotation, eddy current probe 100 is automatically moved or indexed to the next scan line in the indexing direction in accordance with the determined profile. In the exemplary embodiment, the first scan line begins at zero degrees, and each subsequent scan line is registered to this point. The scan of the component proceeds until the scan plan is completed.

The scan data is then analyzed to generate at least one image of the component being scanned includes collecting the signals, i.e. scan data, transmitted from eddy current probe 100 after the scan plan is completed, and combining the scan data into at least one two-dimensional (2D) image for analysis. In the exemplary embodiment, the 2D image includes a combination of the signals transmitted from eddy current probe 100 from both the inspection zones and those produced by the interrupted gaps between them. In addition, the 2D image also includes a plurality of edge signals generated from both sides of the inspection zone. For example, when eddy current probe 100 passes an edge of the component, i.e. from air to material, or vice versa, eddy current probe 100 generates a signal that is typically greater than a signal that is generated by the component material, and is therefore generally interpreted by eddy current probe 100 as a material abnormality. To facilitate reducing or minimizing the imaging effects of these signals, the 2D image is divided into a plurality of sub-images that have approximately the same shape. The sub-images are then sent through a registration and subtraction process to minimize the unwanted signals from gaps and edges.

In the exemplary embodiment, filters based on the characteristic crack signatures of the tested component are then applied to the resulting images to facilitate optimizing the segmentation of significant indications from any remaining noise. In the exemplary embodiment, the matched filter is applied to the 2D image data, to facilitate detecting very small indications, down to approximately 10 mil in length.

The eddy current inspection system described herein generates a scanplan, i.e. the motion control and data acquisition program for the inspection system, scans the component according to the scanplan utilizing a differential eddy current probe, and analyzes the scan data. Accordingly, the method and apparatus described herein facilitate enabling interrupted features of a component to be inspected in a continuous fashion, thereby minimizing the amount of time needed to acquire and process the data compared to known eddy current inspection systems, without having any adverse affects on the sensitivity of the inspection. Moreover, the eddy current inspection system and probe described herein facilitate inspecting a component that includes interrupted features because eddy current inspection system 50, differential probe 100 and image analysis provide and inspection that is relatively immune to surface contours and edges.

The above-described methods and apparatus provide a cost-effective and reliable means to facilitate reducing the amount time needed to perform an eddy current inspection on a component under test. Specifically, the method and apparatus described herein facilitates reducing an inspection time and improve an eddy current system performance by utilizing a continuous scan data acquisition method that eliminates the time consuming raster scans typically used in single coils applications. The eddy current probe described herein includes a differential coil that is positioned to minimize sensitivity to orientation and can therefore, maintain consistent image quality and detectability.

Exemplary embodiments of digital eddy current inspection systems are described above in detail. The systems are not limited to the specific embodiments described herein, but rather, components of each system may be utilized independently and separately from other components described herein. Each system component can also be used in combination with other system components. More specifically, although the methods and apparatus herein are described with respect to aircraft engine parts, it should be appreciated that the methods and apparatus can also be applied to a wide variety of components used within a steam turbine, a nuclear power plant, an automotive engine, or to inspect any mechanical component.

While the invention has been described in terms of various specific embodiments, those skilled in the art will recognize that the invention can be practiced with modification within the spirit and scope of the claims.

What is claimed is:

1. A method for inspecting a component having a surface, said method comprising:
    positioning an eddy current probe proximate to the surface of the component at a first position;
    generating a first position indication corresponding to the first position;
    positioning the eddy current probe proximate to the surface of the component at a second position;
    generating a second position indication that is different than the first position indication and that corresponds to the second position;
    interpolating a plurality of discrete probe positions along a curved path between the first position indication and the second position indication;
    generating a scan plan of the surface of the component using the plurality of discrete probe positions; and
    inspecting the surface of the component in accordance with the scan plan using the eddy current probe, the eddy current probe rotatable to facilitate maintaining the eddy current probe in substantially normal alignment and physical contact with the surface of the component during said inspecting.

2. A method in accordance with claim 1 wherein positioning the eddy current probe proximate to the surface of the component at the first position comprises positioning the eddy current probe normal to the surface of the component at the first position, and wherein positioning the eddy current probe proximate to the surface of the component at the second position comprises positioning the eddy current probe normal to the surface of the component at the second position.

3. A method in accordance with claim 1 wherein at least one of the first position indication and the second position indication includes at least one of a local minimum and a local maximum.

4. A method in accordance with claim 1 further comprising:
   moving the eddy current probe along a first scan line during said inspecting; and
   indexing the eddy current probe, during said inspecting, from the first scan line to a second scan line that is different than the first scan line to generate scan data.

5. A method in accordance with claim 4 wherein indexing the eddy current probe to further comprises indexing the eddy current probe to the second scan line in accordance with the scan plan.

6. A method in accordance with claim 4 further comprising utilizing the scan data to generate at least one two-dimensional image of the component.

7. An eddy current inspection system for inspecting a component having a component surface, said system comprising:
   a differential eddy current probe; and
   a computer communicatively coupled to said eddy current probe, said computer configured to:
      position said eddy current probe at a first position proximate to the component surface;
      generate a first position indication corresponding to the first position;
      position said eddy current probe at a second position proximate to the component surface;
      generate a second position indication corresponding to the second position, the first position indication different than the second position indication;
      interpolate a plurality of discrete probe positions along a curved path between the first position indication and the second position indication;
      generate a scan plan of the component surface using the plurality of discrete probe positions; and
      inspect the component surface in accordance with the scan plan by rotating said eddy current probe to facilitate maintaining said eddy current probe in substantially normal alignment and physical contact with the component surface during the inspection.

8. A system in accordance with claim 7 wherein said computer is further configured to:
   position said eddy current probe normal to the component surface to generate the first position indication; and
   position said eddy current probe normal to the component surface to generate the second position indication.

9. A system in accordance with claim 7 wherein said computer is further configured to:
   move said eddy current probe along a first scan line during the inspection; and
   index, during the inspection, said eddy current probe from the first scan line to a second scan line that is different than the first scan line to generate scan data.

10. A system in accordance with claim 9 wherein said computer is further configured to index said eddy current probe to the second scan line in accordance with the scan plan.

11. A system in accordance with claim 9 wherein said computer is further configured to analyze the scan data to generate at least one two-dimensional image of the component.

\* \* \* \* \*

UNITED STATES PATENT AND TRADEMARK OFFICE
CERTIFICATE OF CORRECTION

| | | Page 1 of 1 |
|---|---|---|
| PATENT NO. | : 8,013,599 B2 | |
| APPLICATION NO. | : 10/993467 | |
| DATED | : September 6, 2011 | |
| INVENTOR(S) | : Suh et al. | |

It is certified that error appears in the above-identified patent and that said Letters Patent is hereby corrected as shown below:

In column 1, line 53, delete "encounter a comer" and insert therefor -- encounter a corner --.
In column 9, line 14, claim 5, delete "probe to further comprises" and insert therefor -- probe further comprises --.

Signed and Sealed this
Twenty-eighth Day of February, 2012

David J. Kappos
*Director of the United States Patent and Trademark Office*